(12) United States Patent
Safarian et al.

(10) Patent No.: US 6,171,869 B1
(45) Date of Patent: Jan. 9, 2001

(54) PROCESS FOR DESALTING AND CONCENTRATING PROTEIN-CONTAINING SOLUTIONS

(75) Inventors: Zara Safarian, Brea; Cynthia R. Blessum, Yorba Linda, both of CA (US)

(73) Assignee: Beckman Coulter, Inc., Fullerton, CA (US)

( * ) Notice: Under 35 U.S.C. 154(b), the term of this patent shall be extended for 0 days.

(21) Appl. No.: 08/825,791

(22) Filed: Apr. 8, 1997

(51) Int. Cl.[7] .................................................. G01N 1/18
(52) U.S. Cl. ............................ 436/178; 436/86; 436/174; 436/175; 436/177; 422/101; 210/638; 210/645; 210/650; 210/651; 210/660; 210/681
(58) Field of Search .................................. 436/63, 74, 86, 436/161, 174, 175, 177, 178, 45; 422/72, 101; 210/638, 645, 650, 651, 660, 681

(56) References Cited

U.S. PATENT DOCUMENTS

| | | | |
|---|---|---|---|
| 4,208,187 | 6/1980 | Givner | 436/521 |
| 4,486,282 | * 12/1984 | Bier | 204/529 |
| 4,522,725 | 6/1985 | Koyama et al. | 210/639 |
| 4,755,301 | * 7/1988 | Bowers et al. | 210/650 |
| 4,769,145 | * 9/1988 | Nakajima | 210/321.75 |
| 4,794,088 | 12/1988 | Miyaki et al. | 436/161 |
| 5,045,196 | 9/1991 | Fang | 210/278 |
| 5,278,288 | * 1/1994 | Kawasaki et al. | 530/361 |
| 5,348,658 | 9/1994 | Fuchs et al. | 210/656 |
| 5,492,834 | 2/1996 | Liu et al. | 436/63 |
| 5,552,325 | * 9/1996 | Nochumson et al. | 436/177 |

FOREIGN PATENT DOCUMENTS

| | | | |
|---|---|---|---|
| 2304603 | * | 3/1997 | (GB) . |
| 54-016380 | * | 2/1979 | (JP) . |

OTHER PUBLICATIONS

Jelkmann et al. *Analytical Biochemistry*, vol. 75, pp. 382–388, 1976*

"A simple method for desalting and concentration of microliter volumes of protein solutions with special reference to capillary electrophoresis," S. Hjertén et al., J. Cap.Elec. 001:1 1994.

"A Rapid Method of Concentrating Proteins in Small Volumes with High Recovery Using Sephadex G–25," A. Saul et al, Analytical Biochemistry 138, 451–453 (1984).

"A Method for Concentrating Dilute Solutions of Macromolecules," H.G. Vartak et al., Analytical Biochemistry 133, 260–263 (1983).

"Identification and quantitation of human urine proteins by capillary electrophoresis," M. Jenkins et al., Journal of Chromatography B, 662 (1994) 108–112.

* cited by examiner

*Primary Examiner*—Maureen M. Wallenhorst
(74) *Attorney, Agent, or Firm*—William H. May; Margaret A. Kivinski

(57) ABSTRACT

Protein-containing solutions requiring desalting and concentration are desalted and concentrated in a one step procedure. Ion exchange and ion retardation resins are used for desalting. A standard ultrafiltration device is modified to contain a mixed bed ion exchange resin and an ion retardation resin. The sample is introduced to the modified ultrafiltration unit and subjected to centrifugation. The centrifugal force drives low molecular weight constituents through the ultrafiltration membrane and draws liquid containing ion exchange products away from contact with the combined resins thereby driving the reaction to achieve a more complete desalting and concentration of the proteins in the sample solution. The proteins in the sample are thus concentrated and desalted simultaneously. The method is useful for concentrating urinary proteins for further analysis, for example, by capillary zone electrophoresis, or other methods which require concentration of the proteins and which are affected by the presence of salts and other low molecular weight ions.

18 Claims, 6 Drawing Sheets

PROCESS FOR DESALTING AND CONCENTRATING PROTEIN-CONTAINING SOLUTIONS

FIELD OF THE INVENTION

The present invention relates generally to processes for preparing protein-containing solutions for subsequent analysis using sample component separation techniques. More particularly, the present invention involves a one-step procedure for desalting and concentrating protein-containing solutions including a method for removing low molecular weight components processed in an ultrafiltration device while concentrating higher molecular weight components.

BACKGROUND OF THE INVENTION

The analysis of protein-containing solutions, in particular biological samples, often requires desalting of the solution for the removal of components that interfere with subsequent analytical techniques. Analytical techniques which may require desalting of sample solutions include those using component separation technologies such as electrophoresis, high performance liquid chromatography (HPLC) and mass spectrometry. Analysis of biological samples containing proteins using capillary electrophoresis, for instance, can be affected by the presence of various low molecular weight salts and protein degradation products. The presence of salts and other low molecular weight ions can increase the ionic strength of a sample to such an extent that the resolution upon electrophoresis decreases dramatically and/or the interpretation of the electropherograms becomes complicated due to the appearance of false peaks.

In addition to desalting, concentration of the sample is also often required since the particular component of interest may be present in small quantities. Frequently, the presence of a particular component in the sample will go undetected unless the component is concentrated to a level that is capable of being detected by the subsequent analytical technique. In the case of capillary electrophoresis, the concentration of the component in the sample may need to be substantially increased for the peak corresponding to the component on the electropherogram to be detectable.

The presence of proteins in samples of biological fluid, such as blood, serum, plasma, cerebrospinal fluid, tear, sweat, saliva and urine is a useful indicator of the presence or absence of certain disease states. Thus, the ability to identify and quantitate a variety of proteins in biological fluid can provide diagnosticians with information which may lead to the diagnosis of a variety of diseases. For example, determination of the urinary excretion of albumin, IgG, free protein human complex-forming glycoprotein (HC), alpha-1-macroglobulin, and kappa and lambda light chains allows in most cases for the classification of proteinuria in the clinically important categories. Using information obtained from the analysis of urine samples, for example, proteinuria may be classified as selective glomerular, unselective glomerular, tubular glomerular, or nontubular glomerular. The presence or absence of Bence Jones proteinuria may also be demonstrated.

The identification of monoclonal free light chains, or Bence Jones protein (BJP), is also important in the assessment of patients with multiple myeloma. Multiple myeloma may be characterized by the presence of BJP in the urine or serum. Approximately 13% of myeloma patients, however, have no BJP in their serum. Therefore, it is essential that both serum and urine be examined for the presence of BJP. The type of light chain present in the urine or serum sample may have a considerable effect on the clinical course of myeloma. For instance, lambda-type light chains are known to accompany rather aggressive myeloma, and exert their toxic effects in a shorter time than do kappa-type light chains.

Generally, identification of free light chains in urine is accomplished by analysis of urine samples with immuno-electrophoresis (IEF) or immunofixation electrophoresis (IFE). Both of these methods are labor intensive and require long execution times. Improved methods for identifying free light chains in urine involve capillary electrophoresis of samples in which the proteins of interest are subtracted from solution by being first fixed to a solid phase through antigen-antibody binding prior to electrophoresis. The identification of the specific proteins is established by their absence from the separated sample. This method is known as immunofixation electrophoresis by immunosubtraction, or IFE/s.

It is often preferable to use an instrument to analyze protein-containing solutions. The instrument should be capable of performing both routine serum protein electrophoresis (SPE) and follow-on, IFE/s testing to characterize monoclonal components detected in the initial SPE screening. One such instrument is the Paragon CZE™ 2000, available from Beckman Instruments, Inc., Fullerton, Calif. The Paragon CZE is a clinical, multi-channel automated capillary electrophoresis instrument. The unit is a dedicated analyzer for SPE and IFE testing, so that many of the traditional capillary electrophoresis parameters such as injection time, capillary rinse sequence and wash times, applied voltage, and absorbance wavelength selection have been optimized and automated to provide walk-away capability. Additional automated and optimized parameters of this instrument include sample volume in primary tubes, sample dilution and additional dilution with solid support. Using the Paragon CZE™ 2000 analyzer, the technique of immunosubtraction is used to remove a specific immunoglobulin class or type from a serum sample.

Regardless of the method used to identify proteins in solutions, and particularly urine, pretreatment of the solution to desalt and concentrate proteins in the sample solution is required. There are several classical methods for desalting or concentrating protein-containing solutions. These methods include dialysis, molecular sieve chromatography, diafiltration, ultrafiltration, precipitation, ion exchange, freeze drying, partitioning between two aqueous polymer phases, osmotic removal of water and reverse phase HPLC. These methods typically consist of two separate steps for desalting and concentration and may require specialized equipment and procedures associated with each step of desalting and concentration.

Gel filtration is one useful and mild method for desalting a protein-containing solution. The gel used in gel filtration processes consists of an open, cross-linked, three-dimensional molecular network, which can be cast in bead form for column packing and optimum flow characteristics. Pores within the beads are of such sizes that they are not accessible by large molecules, but smaller molecules can easily penetrate all the pores. Gel filtration media beneficially exhibit little protein binding and give high recoveries for even small amounts of proteins. Some of the most commonly used gel filtration support are Sephadex G-25 and BioGel P-30. Although gel filtration has many advantages, this method has several features which make it inapplicable for use in, for example, an ultrafiltration device. The primary problem with gel filtration media, particularly with polyacrylamide beads, is their softness. Even very gentle pressure, including osmotic pressures obtained during chromatography, can cause distortion, irregular packing and poor flow characteristics. Recently, Bio-Rad introduced the Bio-Spin chromatography column which is prepacked with a polyacrylamide gel matrix (Bio-Gel P-6). This ready-to-use column can be used for rapid desalting of a protein mixture at low centrifugal forces. Desalting in this manner, however, is only applicable for very small sample volumes and column volumes. Proper matrix preparation and column packing are required. The degree of desalting is further dependent on the column dimensions, shape and total volume. The optimal removal of salt that can be expected is achieved with sample volumes not exceeding 20–25% of the column volume.

Desalting of simple protein-containing solutions is often accomplished with ion exchange using, for example, a mixed bed resin. Commercially available mixed bed resins, such as IonClear BigBead (Sterogene Bioseparations, Inc., Arcadia, Calif.), AG 501-X8 (Bio-Rad, Hercules, Calif.) and Duolite mixed bed resin (BDH Laboratories, Poole, England; distributed by Gallard-Schlesinger Industries, Inc., Carle Place, N.Y.), are suitable for capturing both cations and anions from protein-containing solutions. Large bead size and surface modifications provide high capacity binding of small ions but very low capacity for much larger protein molecules. A mixed bed resin can be used in a packed bed column or mixed with the process feed to adsorb ions in the batch mode. In the case of complex biological samples, however, the pH of the sample treated with mixed bed resin can turn acidic and protein precipitation may occur. Accordingly, mixed bed resins are not suitable for the desalting of urine samples.

Another method for removal of salts from protein-containing solutions using ion exchange is accomplished using ion retardation resins. Methods using ion retardation resins, such as AG 11 A8 Resin (Bio-Rad, Hercules, Calif.) employ a different mechanism than conventional ion exchange in which salt uptake occurs via an actual exchange of ions. In the method using ion retardation resin, salts are adsorbed without an exchange of ions. The AG 11 A8 ion retardation resin has the ability to strongly bind hydrogen ions.

Jelkmann and Bauer used ion exchange chromatography with ion retardation AG 11 A8 Resin and mixed bed resin (AG 501-X8, Bio-Rad) to desalt and remove 2,3-diphosphoglycerate (DPG) from human hemoglobin. Jelkmann, W., Bauer, C., What is the Best Method to Remove 2,3-Diphosphoglycerate from Hemoglobin?, Analytical Biochemistry, 75, 382–388, 1976. They consequently used two columns with ion retardation and mixed bed resin to achieve this goal. The procedures involved multiple washing and eluting steps which are very time consuming.

Diafiltration is another method for desalting and concentrating protein-containing solutions. However, a one-step diafiltration process does not provide complete desalting. Only with multiple steps of diafiltration and changing buffers can one achieve the complete desalting necessary to analyze protein-containing solutions such as urine samples using capillary electrophoresis.

Hjerten et al. disclose a procedure for desalting and concentrating small volumes of biological samples, including urine. Hjerten et al., A Simple Method for Desalting and Concentration of Microliter Volumes of Protein Solutions with Special Reference to Capillary Electrophoresis, J. Cap. Elec. 1, 83–89, 1994. The method involves contacting microliter volumes of a sample with a polyacrylamide gel having a specified pore size and includes steps for preparation of the gel. The method yields a twenty-fold increase in protein concentration of the sample solutions. The combination of small sample yield and relatively low concentration increase after desalting and concentration makes this procedure impractical for the detection of proteins in protein-containing solutions which require 50–100 fold increase in concentration. The method is also inapplicable to automated systems for the analysis of proteins, particularly capillary electrophoresis instruments.

There is, accordingly, a need for a simple and efficient method for desalting and concentrating protein-containing solutions. A method is needed to remove irrelevant interfering compounds and concentrate proteins in the sample solutions for further analysis, for example, by capillary electrophoresis. In particular, a simple method for the desalting and concentration of urine proteins in a sample which is compatible with the subsequent analysis of the urinary proteins in a sample using an automated electrophoresis instrument is needed.

SUMMARY OF THE INVENTION

The present invention meets the above needs. A simple, one-step procedure is provided which simultaneously desalts and concentrates a protein-containing solution. The process of the present invention first comprises modifying an ultrafiltration device to contain an ion exchange resin, and preferably an equal amount of an ion retardation resin. The protein-containing solution to be desalted and concentrated is then added to the ultrafiltration device containing the ion exchange and ion retardation resins. The ultrafiltration device is subjected to centrifugation and, in one step, the sample solution is desalted and concentrated.

The desalting and concentration process of the present invention is enhanced by the application of centrifugal force. Upon the application of centrifugal force, desalted solution flows through a semipermeable membrane of the ultrafiltration device having a defined range of pore size. The desalted solution is thus removed from contact with the mixed bed and ion retardation resins which drives the reaction by continuously removing reaction products ($H^+$ and $OH^-$) from the resin. A more complete ion exchange is thus provided between the solution and the resin than prior methods.

The method of the present invention yields desalted sample solutions having as high as a 100-fold increase in protein concentrations. Desalted and concentrated sample solution recovered from the ultrafiltration device can be analyzed using capillary electrophoresis or other analytical technique. The present invention is particularly suited for the desalting and concentration of proteins in a urine sample to be measured by capillary electrophoresis.

BRIEF DESCRIPTION OF THE DRAWINGS

FIG. 1(*b*) is an electropherogram of the same untreated urine sample on an expanded scale.

DETAILED DESCRIPTION OF THE PREFERRED EMBODIMENTS

Figure 1A:
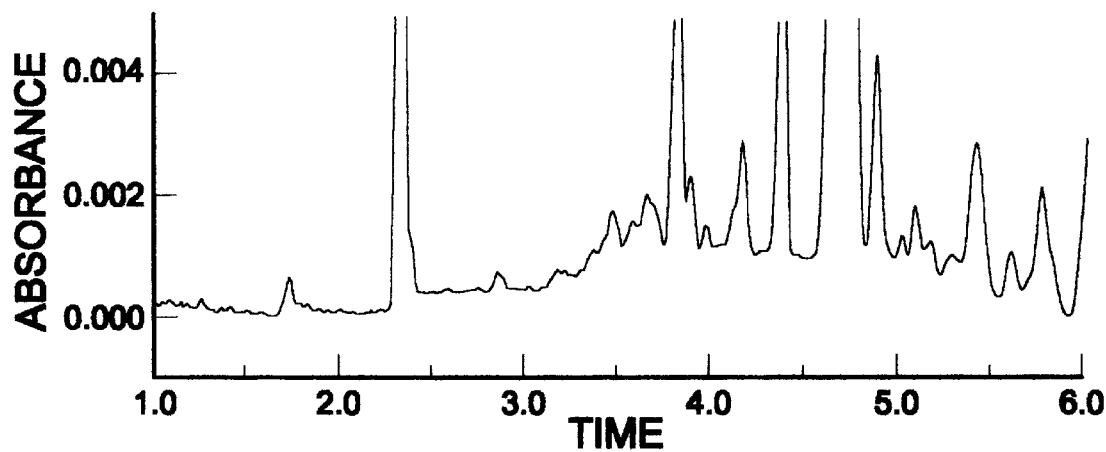
FIG. 1(*a*) is an electropherogram of an untreated urine sample.

In an embodiment of the present invention a procedure for desalting and concentration of a protein-containing solution is provided wherein the sample is desalted and concentrated in a single step. The process comprises modifying an ultrafiltration device to contain an ion exchange resin, and preferably an ion retardation resin, adding a protein-containing solution to the ultrafiltration device, subjecting the modified ultrafiltration device to centrifugation and recovering a concentrated and desalted sample solution from the ultrafiltration device. The centrifugation of the protein-containing solution in the ultrafiltration device containing ion exchange and ion retardation resins is the single step for desalting and concentration which replaces the previously required separate procedures for desalting and concentrating proteins in a sample solution.

The medium for desalting the protein-containing solution in accordance with an embodiment of the present invention can be an ion exchange resin. Ion exchange resins are commonly polymers, for example, a styrene divinylbenzene co-polymer, with attached ionic groups. A convenient form of the resin for use in an embodiment of the present invention is a spherical bead, although any form of resin can be used. The ionic group attached to the resin is an electrolyte, one ion of which is fixed to the resin while the other, of opposite charge, is mobile. A cation exchange resin exchanges its mobile cation for other cations present in the solution around the resin, whereas, an anion exchange resin exchanges its mobile anions for other anions. There is a competition of ions in the sample solution for the exchange sites of the resin. The resulting equilibria is influenced by usual equilibria factors, for example, concentration and mobility of each ion, and time.

The ion exchange resin of the present invention is preferably a mixed bed ion exchange resin. Mixed bed resins are a mixture of anion ($OH^-$) and cation ($H^+$) exchange resins having different densities, which facilitates regeneration of the resin. As a result of the exchange of ions, pure water is produced. Mixed bed resins can provide a method for protein deionization. Salts, calcium ions and heavy metal ions can be removed from protein solutions using mixed bed resins.

The particular properties of the mixed bed resin can affect the performance of the desalting procedure. The capacity of the mixed bed resin to bind small ions is preferably high, but much larger protein molecules should not bind. A relatively large bead size and surface modifications can prevent non-specific binding of proteins. In the present invention, the preferred mixed bed resin is capable of binding low molecular weight anions and cations having a molecular weight of 1000 Daltons or less, although mixed bed resins capable of binding molecular weight anions and cations having molecular weights above 1000 Daltons can also be used. The mixed bed resin will preferably bind low molecular weight anions in the sample and exchange the low molecular weight anions for hydroxyl ions. The low molecular weight cations in the sample will preferably be bound and exchanged for hydrogen ions. The desalting or ionic contaminant removal aspect of the present invention can be achieved using a commercially available mixed bed resin, such as IonClear BigBead (Sterogene Bioseparations, Inc., Arcadia, Calif.).

The pH of the sample during the desalting and concentration process of the present invention is preferably maintained above about 7.0 and most preferably between about 7.0 and about 8.0. Variations in the pH within some urine samples can cause protein denaturation and precipitation. The pH of the sample can be beneficially maintained at a pH level between about 7.0 and about 8.0 during the desalting and concentrating of the sample by including ion retardation resin along with the mixed bed resin added to the ultrafiltration device. In this aspect of the invention, the desalting or ionic contaminant removal of the sample is achieved using a mixture of mixed bed resin and ion retardation resin.

An example of an ion retardation resin is a rigid, cross-linked styrene divinylbenzene polymer lattice with attached quaternary ammonium groups, which are strongly basic anion exchange groups. Trapped within the rigid polymer lattice there is woven a linear and relatively flexible acrylic polymer having carboxyl groups, which are weakly acidic cation exchange groups. Thus, each resin bead is a molecular mixture of a cation and anion exchanger. Inorganic ions, such as salts, are adsorbed without ion exchange. The hydrogen ion of the ion retardation resin is so strongly held by the carboxyl group that it is not eluted with water. A commercially available ion retardation resin which can be used in accordance with an embodiment of the present invention is AG 11 A8 (Bio-Rad, Hercules, Calif.).

In a preferred embodiment of the present invention, equal amounts by weight of mixed bed resin and ion retardation resin are placed into an ultrafiltration device. A sample solution containing proteins is simultaneously desalted and concentrated upon adding the sample to the ultrafiltration device containing the mixed bed and ion retardation resins and subjecting the ultrafiltration device to centrifugation. The amount of sample which can be desalted and concentrated using a given amount of resin can vary, however, in preferred embodiments the ratio of the volume of the sample added to the ultrafiltration device to the total weight of resin is between about 1:2 to 1:4, most preferably about 1:2.

The simultaneous desalting and concentration procedure of the present invention is accomplished using a modified ultrafiltration technique. Ultrafiltration techniques use devices such as ultrafilters and rely upon centrifugal or other driving force to separate components within the sample through a structure such as a membrane. Smaller molecular size components in the sample pass through pores of the membrane whereas larger molecular size components do not. The size of the pores of the membrane is one of the features that determines the degree of separation that can be achieved during the ultrafiltration process.

Any ultrafiltration device can be used to practice the present invention, although it is preferred that the ultrafiltration device have a molecular weight cut-off (MWCO) of 10,000 Daltons or higher. Suitable ultrafiltration devices are commercially available from Millipore Corp., Bedford, Mass., or LifeScience Purification Technologies, Acton, Mass.

An ultrafiltration device generally has an upper section which acts as a receptacle for receiving a sample, and a lower section which comprises a membrane. Upon centrifugation, sample fluid passes from the upper section to the lower section and contacts the membrane. Lower molecular weight components pass through the membrane and into a collection tube. The higher molecular weight components, such as proteins, do not pass through the membrane and are collected in a concentrate pocket in the lower section of the ultrafiltration device.

In accordance with embodiments of the present invention, resin is placed in the ultrafiltration device, for example, in the receptacle in the upper section of the ultrafiltration device for receiving the sample. The resin can be added to the ultrafiltration device in the form of beads added directly to the ultrafiltration device, or, in the alternative, the resin can be placed in a separate container capable of being placed inside the receptacle in the upper section of the ultrafiltration device. In this embodiment, the container holding the resin has openings through which the sample is allowed to pass through the container and into the ultrafiltration device, but the resin beads remain in the container. The container containing the resin is placed inside the ultrafiltration device and sample is added. The sample interacts with the resin and ions in the sample solution are exchanged for ions on the resin. Upon centrifugation, the sample is forced through the upper region of the ultrafiltration device and into contact with the membrane comprising the lower region of the ultrafiltration device. Smaller molecules pass through the membrane while the larger molecules are collected in the concentrate pocket. The concentrated and desalted sample is then collected from the collection pot in the ultrafiltration device.

The method of the present invention can be used to desalt and concentrate proteins in sample solutions for subsequent analysis. The concentration of the proteins in a sample solution treated in accordance with embodiments of the present invention can be increased by up to one hundred times or more. Substantially all of the salts and UV absorbing low molecular compounds are also removed. The analysis of proteins in samples desalted and concentrated by methods of the present invention can advantageously be accomplished using an electrophoresis instrument such is the Paragon CZE™ 2000 (Beckman Instruments, Inc.).

The protein-containing solutions that are desalted and concentrated in accordance with embodiments of the present invention are preferably samples of biological fluid. The biological fluid can be selected from urine, serum, semen, whole blood, cerebrospinal fluid or other biological fluid in which the presence of proteins is a useful diagnostic indicator. Urine is a particularly useful biological fluid for this purpose since the presence of proteins, and specifically kappa and lambda light chains, is indicative of multiple myeloma.

The detection of proteins in a biological sample desalted and concentrated in accordance with embodiments of the present invention can be accomplished using any number of methods. A preferred method of analyzing proteins in a biological sample is immunofixation electrophoresis, or IFE. A most preferred method further utilizes the technique of immunosubtraction. Immunofixation electrophoresis by immunosubtraction (IFE/s) is a method that allows the identification of specific peaks in an electropherogram. Samples are incubated with solid supports containing immunological binding partners for the components of interest. The solid supports used in the present method contain specific antibodies which selectively bind monoclonal components in the biological sample, e.g., IgG, IgA, IgM, heavy chains and lambda and kappa light chains. After incubation with the solid phase, the specific components in the sample are fixed by the specific solid phase ligand and are removed from the sample which is subjected to electrophoretic separation. Comparison of the electropherograms of samples with and without fixation shows a reduction of the pattern peak corresponding to the fixed moiety. The type of monoclonal components can be identified by comparing the electropherograms from the sample exposed to the various solid supports to that of an untreated control and visually determining which solid support removed the abnormal protein.

The following non-limiting examples illustrate the various advantages of the present invention. It is understood that these examples are for illustration purposes only and that alternative embodiments such as the use of alternative analytical techniques are contemplated as within the scope of the present invention.

EXAMPLE 1
Desalting of Urine Samples

The level of desalting was checked by measuring the conductivity and pH of urine samples, or by analyzing the samples on a capillary electrophoresis instrument for the presence of small molecular weight interfering components. The capillary electrophoresis instrument used was a Paragon CZE™ 2000 (Beckman Instruments, Inc.). Concentration of kappa and lambda light chains in the urine samples were checked before and after the desalting and concentration step.

Figure 1B:
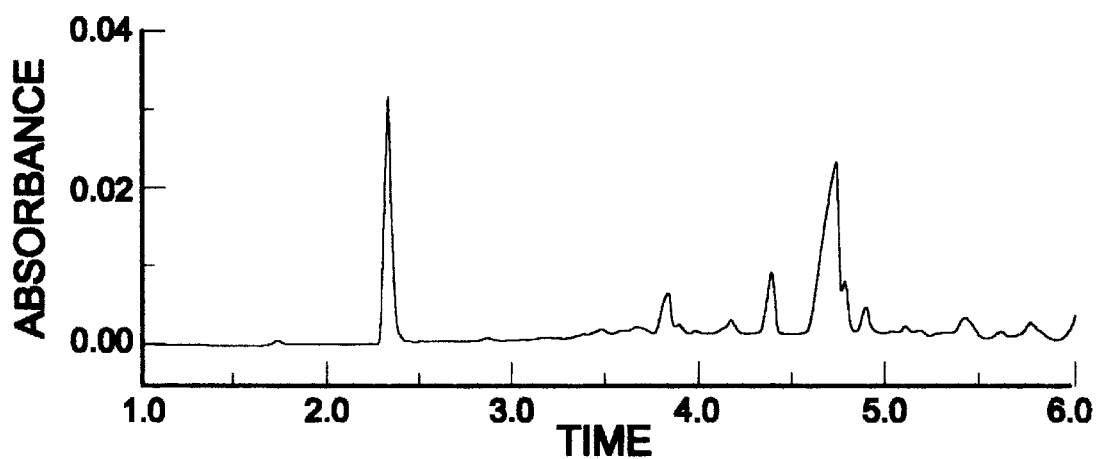

FIG. 1 shows the capillary electrophoresis profile for an untreated urine sample. FIG. 1(a) is on a normal scale and FIG. 1(b) is on an expanded scale. These electropherograms clearly show the presence of biological components in large quantities. The large number of peaks are presumably due to small molecules, such as creatinine and urea, and protein breakdown products, such as peptides and amino acids. Constituents found at low concentrations are not detectable on these electropherograms. The concentration of lambda light chain was determined to be 10 mg/dl. The pH of the sample was 6.6 and the conductivity of the sample was 19.5 mS.

Figure 2A:
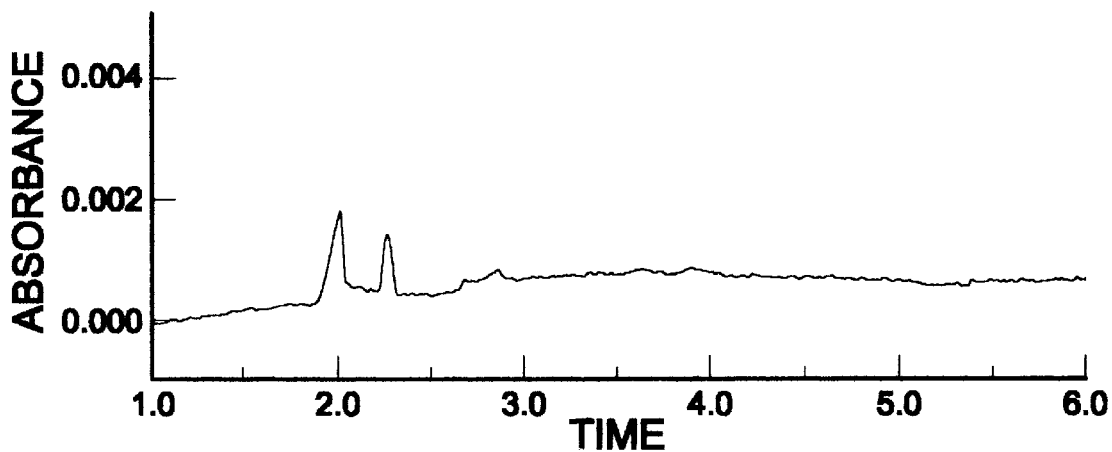
FIGS. 2(*a*) and 2(*b*) shows electropherograms of urine samples after desalting only.
Figure 2B:
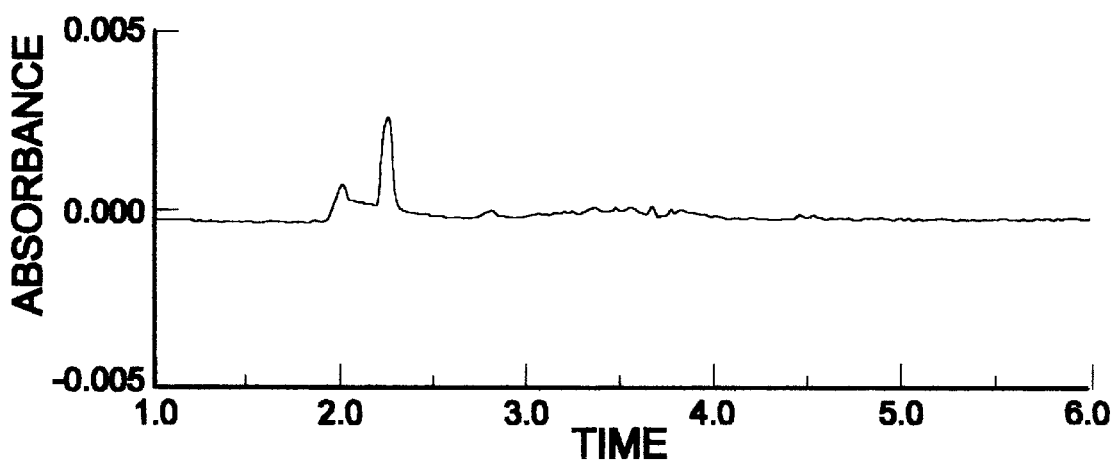

In order to remove interfering substances, the untreated urine sample was subjected to desalting techniques. FIG. 2(a) shows an electropherogram of the sample after desalting with an EconoPak 10DG column based on size exclusion (Bio-Rad). FIG. 2(b) shows the electropherogram of the sample desalted with IonClear BigBead mixed bed resin in combination with AG 11 A8 ion retardation resin in a batch method. The conductivity of the sample was 0.11 mS and the pH was 7.9. Both electropherograms show the presence of only two system peaks. No interfering peaks were detected. Proteins were undetectable, however, because the concentration of the proteins was below the lower limit of detection of the instrument.

EXAMPLE 2
Concentration of Urine Samples Via Ultrafiltration

Figure 3A:
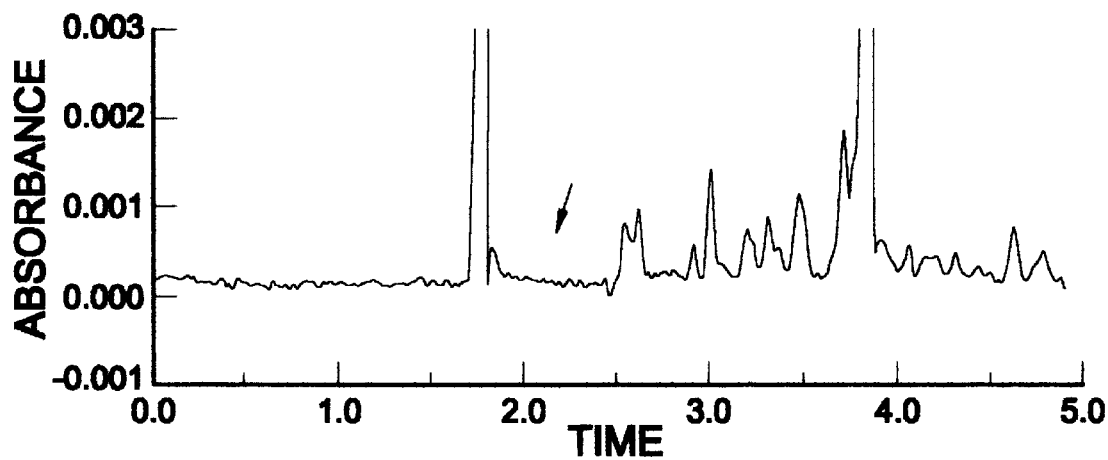
FIGS. 3(*a*) and 3(*b*) shows electropherograms of an untreated urine sample and a urine sample after ultrafiltration only.
Figure 3B:
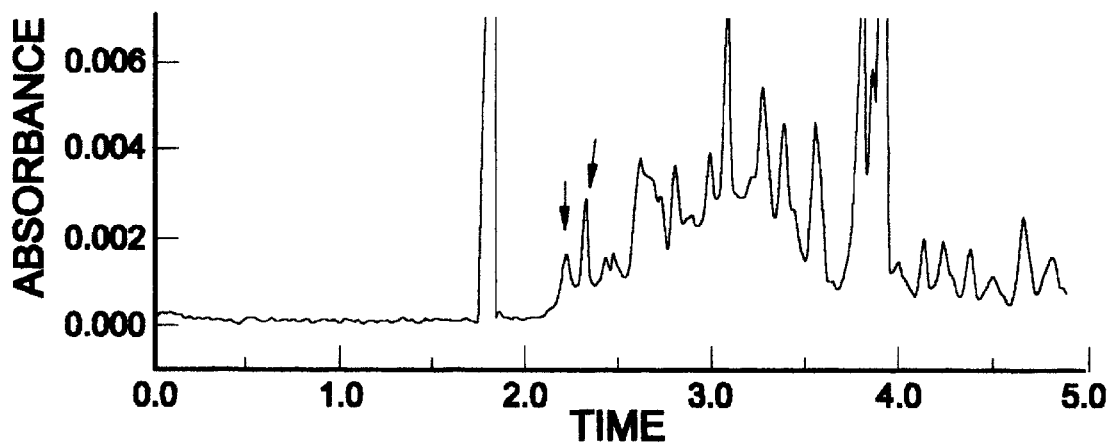

FIG. 3(a) shows the capillary electrophoresis profile of a neat (untreated) urine sample. FIG. 3(b) shows the capillary electrophoresis profiles for a urine sample subject to ultrafiltration using a Vivaspini 15 ultrafiltration device (LifeScience Purification Technologies, Acton, Mass.). Two new protein peaks became detectable in the electropherogram of the concentrated sample, whereas no false peaks were observed in the electropherogram of the neat sample. Other low concentration constituents remained undetectable, however, due to incomplete desalting and the presence of many other interfering compounds.

EXAMPLE 3
Desalting and Concentration of Urine Samples Via a One-Step Procedure 3.8 grams of IonClear BigBead mixed bed resin (Sterogene) and 3.8 grams of AG 11 A8 ion retardation resin (Bio-Rad) were weighed and placed into an ultrafiltration device having a molecular weight cutoff of 10,000 Daltons (Millipore Corp. or LifeScience Purification Technologies).

A 15 ml urine sample was added to the ultrafiltration device. The mixture was gently stirred for approximately 5 to 10 minutes using a Multi-purpose Rotator, Model 151 (Scientific Industries, Bohemia, N.Y.).

Figure 4A:
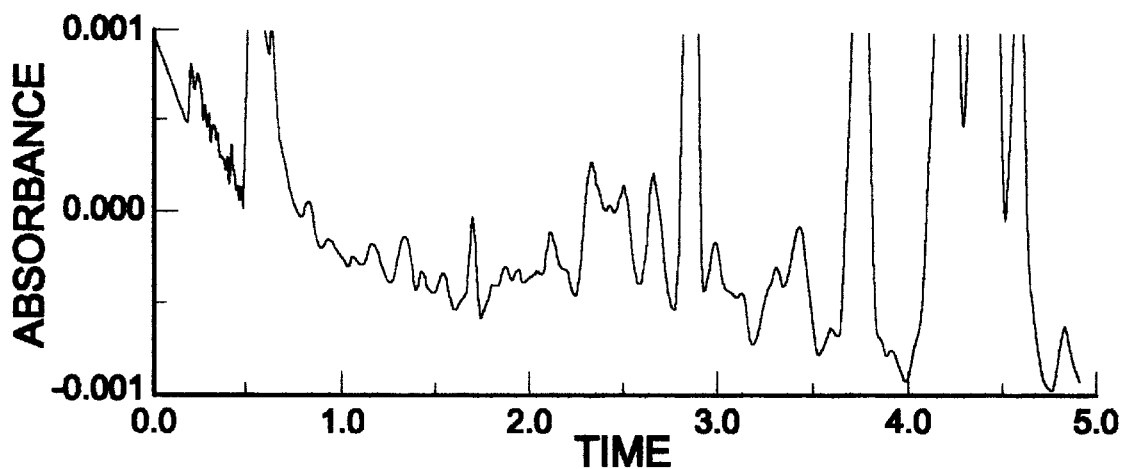
FIGS. 4(*a*) and 4(*b*) shows electropherograms of an untreated urine sample and a urine sample desalted and concentrated in a one-step procedure in accordance with an embodiment of the present invention.
Figure 4B:
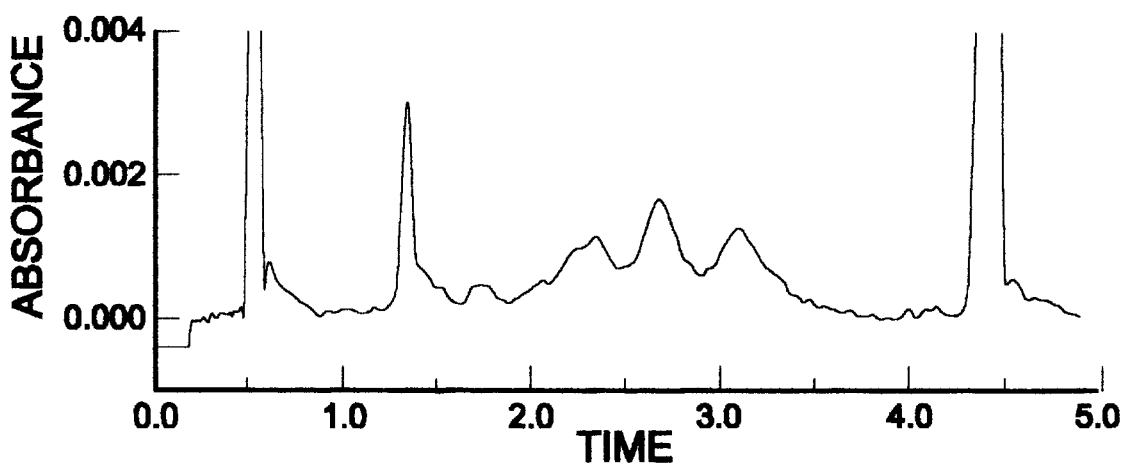

The ultrafiltration device was subjected to centrifugation using a Model J-6B Centrifuge (Beckman Instruments, Inc., Fullerton, Calif.) at up to 2000×g for 30 to 35 minutes until the retentate sample was one-hundredth of its original volume. The desalted and concentrated sample was then pipetted from the concentrate pocket of the ultrafiltration device and transferred to sample cups. FIG. 4(b) is the electropherogram of the urine sample desalted and concentrated in the one-step procedure in accordance with the present invention. The treated sample was clear, without protein precipitation. Due to the one-step desalting and concentration procedure, the protein peaks were easily detectable without the presence of any interfering components in the electropherogram as compared with the electropherogram of the neat urine sample, shown in FIG. 4(a).

EXAMPLE 4
Analysis of Desalted and Concentrated Urine Samples

Desalted and concentrated urine samples were analyzed on an automated capillary electrophoresis system, the Paragon CZE™ 2000 (Beckman Instruments, Inc.), for protein separation and identification of free light chain gamma globulins. The capillary electrophoresis instrument is advantageously automated and capable of performing both routine serum protein electrophoresis (SPE) and follow-on testing to characterize monoclonal components detected in the initial SPE screening.

Desalted and concentrated urine samples containing Bence Jones proteins (kappa and lambda light chains) to be detected were treated with two solid supports, each containing an immunoglobulin specific binding partner for the light chains (kappa and lambda). The urine samples treated with each solid support were then analyzed by capillary electrophoresis along with the untreated sample as a control.

Buffer solution was used to equilibrate the capillaries on the capillary electrophoresis instrument. The desalted and concentrated urine sample was pre-diluted with sample diluent (Signal Reagent, Beckman Instruments, Inc.). The pre-diluted sample was added to a control vial and to two different solid supports, one containing an anti-kappa light chain antibody, the other containing an anti-lambda light chain antibody. The samples and the solid supports were mixed. The samples and the control were run on the capillary electrophoresis instrument simultaneously and the absorbance of the proteins in the samples were measured.

The capillaries were washed and rinsed with buffer solution.

Figure 5A:
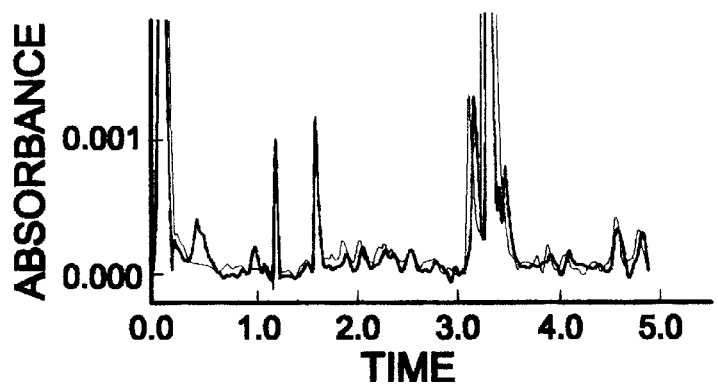
FIG. 5(a) depicts overlaid electropherograms of an untreated urine sample and a urine sample that has been treated with an anti-kappa light chain antibody solid phase.
Figure 5B:
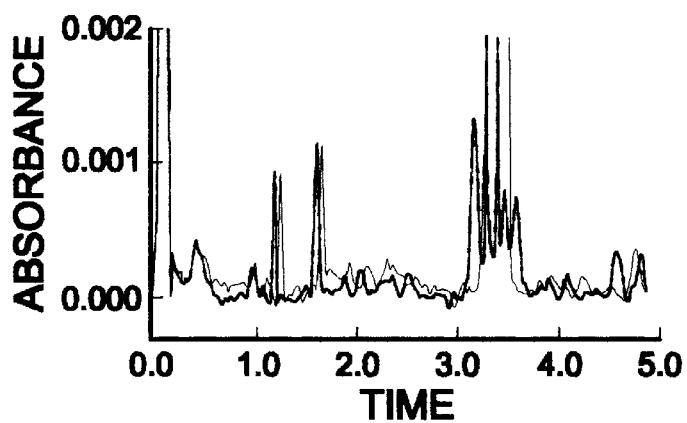
FIG. 5(b) depicts overlaid electropherograms of an untreated urine sample and a urine sample that has been treated with an anti-lambda light chain antibody solid phase.
Figure 5C:
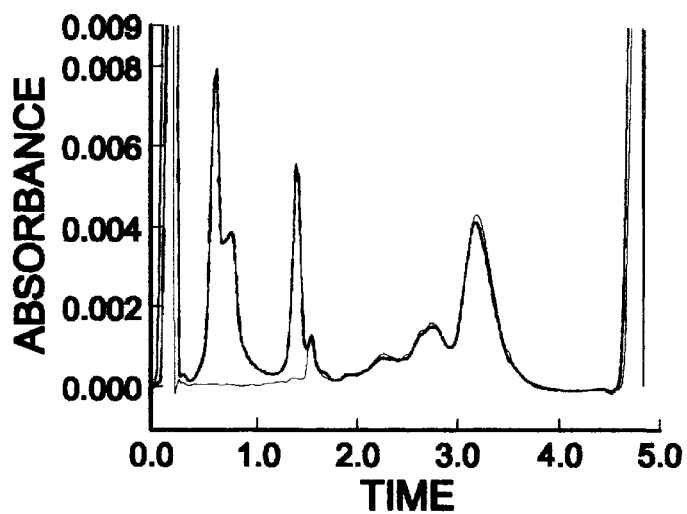
FIG. 5(c) depicts overlaid electropherograms for a neat urine sample and a urine sample that has been desalted and concentrated in a one-step procedure in accordance with an embodiment of the present invention and in which kappa light chain has been identified and immunosubtracted from the sample by treating the desalted and concentrated sample with an anti-kappa light chain antibody solid phase.
Figure 6A:
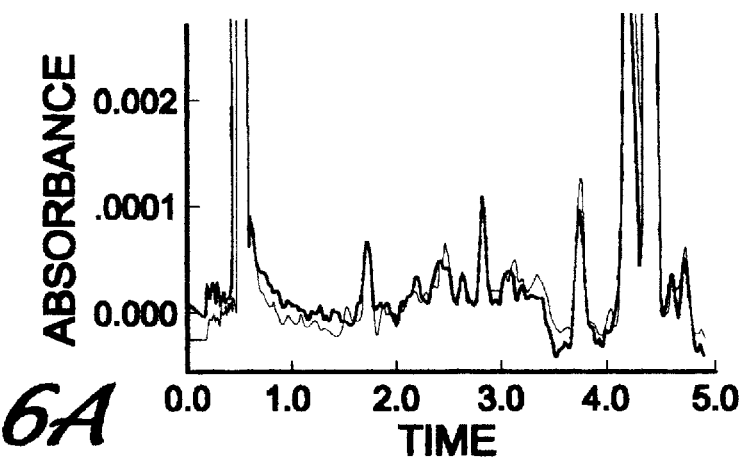
FIG. 6(a) depicts overlaid electropherograms of another untreated urine sample and the same urine sample that has been exposed to an anti-kappa light chain solid support.
Figure 6B:
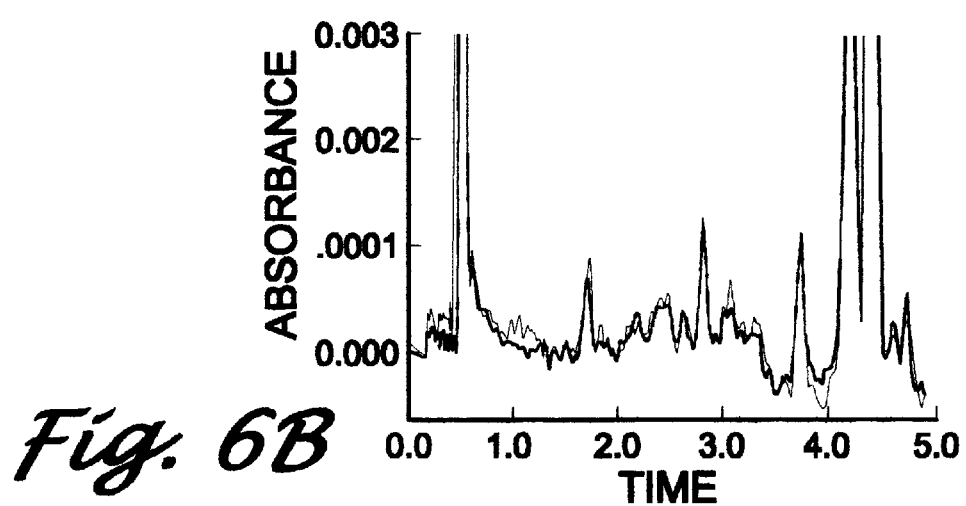
FIG. 6(b) depicts overlaid electropherograms of another untreated urine sample and the same urine sample that has been exposed to an anti-lambda light chain solid support.
Figure 6C:
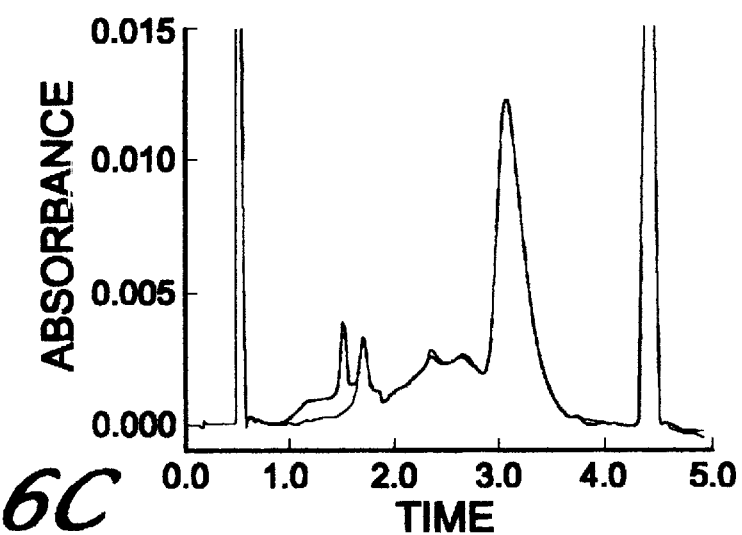
FIG. 6(c) shows overlaid electropherograms of an untreated urine sample and the same urine sample that has been desalted and concentrated in accordance with an embodiment of the present invention and in which lambda light chain has been identified and immunosubtracted from the sample by treating the desalted and concentrated sample with an anti-lambda light chain antibody solid phase.

FIG. 5(a) shows overlaid electropherograms for a neat urine sample, one for the untreated control and one for the portion of the sample exposed to an anti-kappa solid support. FIG. 5(b) shows overlaid electropherograms for a neat urine sample and one exposed to an anti-lambda solid support. FIG. 5(c) shows overlaid electropherograms for a neat urine sample as an untreated control and a sample desalted and concentrated in accordance with embodiments of the present invention and exposed to anti-kappa solid support. Protein peaks were clearly detected in the electropherograms of desalted and concentrated urine samples as compared with the electropherograms of the untreated urine samples. The subtraction of the two peaks with anti-kappa solid support allowed for the identification of light chains in the sample as being of the kappa type. FIGS. 6(a) and 6(b) show overlaid electropherograms of another neat urine sample, one for the untreated control and one exposed to an anti-kappa or anti-lambda solid support, respectively. FIG. 6(c) shows two overlaid electropherograms, one for the untreated control and another desalted and concentrated in accordance with the present invention and exposed to anti-lambda solid support. Only after desalting and concentrating was it possible to detect and identify the light chains in the urine sample as the lambda type.

The present invention is defined by the following claims. We claim:

1. A process for desalting and concentrating a protein-containing solution, wherein the protein-containing solution contains unwanted ions that need to be removed from the solution so that the protein-containing solution is desalted, said process comprising:
   (a) modifying an ultrafiltration device to contain an ion exchange resin for absorbing the unwanted ions contained in the protein-containing solution; (b) adding a protein-containing solution to said ultrafiltration device;
   (c) subjecting said ultrafiltration device to centrifugation to separate the ion exchange resin with absorbed ions from the protein-containing solution and to form a desalted and a concentrated solution; and (d) recovering the concentrated and desalted solution from said ultrafiltration device.

2. The process of claim 1, wherein said ion exchange resin is a mixed bed ion exchange resin.

3. The process of claim 2, wherein said mixed bed ion exchange resin is capable of binding low molecular weight anions and cations having a molecular weight of no more than 1000 Daltons, and wherein said mixed bed ion exchange resin binds low molecular weight anions and cations present in said protein-containing solution and exchanges said low molecular weight anions and cations in said protein-containing solution for hydroxyl and hydrogen ions, respectively.

4. The process of claim 1, wherein said ultrafiltration device comprises a membrane having a molecular weight cutoff of 10,000 Daltons.

5. The process of claim 1, wherein the protein-containing solution is a biological sample.

6. The process of claim 5, wherein said biological sample is a biological fluid selected from the group consisting of urine, serum, semen, whole blood and cerebrospinal fluid.

7. The process of claim 6, wherein the biological fluid is urine.

8. The process of claim 7, wherein the proteins in said urine sample are kappa and lambda light chains.

9. The process of claim 1 wherein step (a) further comprises modifying said ultrafiltration device to contain an ion retardation resin.

10. The process of claim 9, wherein said ion exchange resin and said ion retardation resin are present in a weight ratio of about 1:1.

11. A process for analyzing a sample containing proteins, wherein the sample contains unwanted ions that need to be removed from the solution so that the sample is desalted, said process comprising:
- (a) placing an ion exchange resin into an ultrafiltration device for absorbing the unwanted ions contained in the sample;
- (b) adding a sample containing proteins to said ultrafiltration device;
- (c) subjecting said ultrafiltration device to centrifugation to separate the ion exchange resin with absorbed ions from the sample and to form a desalted and a concentrated sample;
- (d) recovering the concentrated and desalted sample from said ultrafiltration device; and
- (e) analyzing said concentrated and desalted sample on a capillary electrophoresis instrument.

12. The method of claim 11 wherein said ion exchange resin is a mixed bed resin.

13. The process of claim 12 wherein step (a) further comprises placing an ion retardation resin into said ultrafiltration device.

14. The process of claim 13 wherein said mixed bed resin and said ion retardation resin are present in equal amounts by weight.

15. The process of claim 11 wherein said sample is a biological fluid.

16. The process of claim 15 wherein said biological fluid is urine.

17. A method for desalting and concentrating a urine sample comprising:
- (a) placing an equal amount by weight of a mixed bed resin and an ion retardation resin into an ultrafiltration device;
- (b) adding a urine sample to the ultrafiltration device;
- (c) subjecting the ultrafiltration device to centrifugation; and
- (d) recovering a desalted and concentrated urine sample from the ultrafiltration device.

18. A method for identifying kappa and lambda light chains in a urine sample comprising:
- (a) modifying an ultrafiltration device to contain equal amounts by weight of a mixed bed resin and an ion retardation resin;
- (b) adding a urine sample to the ultrafiltration device;
- (c) subjecting the ultrafiltration device to centrifugation;
- (d) recovering a desalted and concentrated protein solution from the ultrafiltration device,
- (e) treating portions of the desalted and concentrated protein solution with solid supports containing immunological binding partners for kappa and lambda light chains, thereby producing treated portions and untreated portions;
- (f) analyzing the treated and untreated portions of the protein solution on a capillary electrophoresis instrument; and
- (g) comparing electropherograms for the treated and untreated portions of the protein solution and identifying the presence of kappa and lambda light chains by the absence of peaks corresponding to kappa and lambda light chains on the electropherograms for the treated portions.

* * * * *